United States Patent
Mori et al.

(10) Patent No.: US 7,541,050 B2
(45) Date of Patent: Jun. 2, 2009

(54) TWO-LAYERED OLEFIN-BASED RESIN PELLETS FOR INSECTICIDAL RESIN COMPOSITION

(75) Inventors: Hiroyuki Mori, Itami (JP); Sumio Hamada, Itami (JP); Takeshi Okuno, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 277 days.

(21) Appl. No.: 10/595,644

(22) PCT Filed: Nov. 5, 2004

(86) PCT No.: PCT/JP2004/016779

§ 371 (c)(1),
(2), (4) Date: May 2, 2006

(87) PCT Pub. No.: WO2005/044533

PCT Pub. Date: May 19, 2005

(65) Prior Publication Data

US 2007/0134495 A1     Jun. 14, 2007

(30) Foreign Application Priority Data

Nov. 7, 2003    (JP) .............................. 2003-378135

(51) Int. Cl.
*A61K 9/14*     (2006.01)
*B32B 27/32*    (2006.01)
*A01N 53/00*    (2006.01)

(52) U.S. Cl. .................. 424/489; 428/407; 514/531

(58) Field of Classification Search .................. None
See application file for complete search history.

(56) References Cited

U.S. PATENT DOCUMENTS 5,627,218 A * 5/1997 Bradt ........................ 521/57
6,193,990 B1 * 2/2001 Cannelongo ............... 424/408
6,986,945 B2 * 1/2006 Mushiake et al. .......... 428/407

FOREIGN PATENT DOCUMENTS

JP     8-81584 A     3/1996
JP     8-113828 A    5/1996
JP     08302080 A *  11/1996

OTHER PUBLICATIONS

Machine translation of JP-08-302080.*
Machine translation of JP-08-302080, 1996.*
"Handbook of Plastic aids" ($1_{st}$ Edition), Edition by Lv Shiguang, pp. 299-320, pp. 908-910, Light Industry Press, Mar. 31, 1997.
"Methods for Preparing Metal Soap and Use Thereof, Zhang Jinde, Household and Personal Care Chemical Industry", Dec. 31, 1991, vol. 6, pp. 33-35.

* cited by examiner

*Primary Examiner*—Sreeni Padmanabhan
*Assistant Examiner*—Christopher R Lea
(74) *Attorney, Agent, or Firm*—Sughrue Mion, PLLC

(57) ABSTRACT

A two-layered olefin-based resin pellet comprising a core layer formed of an olefin-based resin composition (A) and a sheath layer formed of an olefin-based resin composition (B) and laminated on the outer surface of the core layer, wherein said olefin-based composition (A) contains an insecticidal compound, a granular inorganic filler, a metal soap, and an olefin-based resin (a) having a relatively high solubility to the insecticidal compound; and said olefin-based resin composition (B) contains, as a main component, an olefin-based resin (b) having a relatively low solubility to the insecticidal compound.

4 Claims, 1 Drawing Sheet

TWO-LAYERED OLEFIN-BASED RESIN PELLETS FOR INSECTICIDAL RESIN COMPOSITION

TECHNICAL FIELD

The present invention relates to two-layered olefin-based resin pellets for use in an insecticidal resin composition, an insecticidal resin composition comprising the same as a raw material, and insecticidal filaments made thereof.

BACKGROUND OF THE INVENTION

Insecticidal sheets, insecticidal filaments, etc. made of thermoplastic resins, for example, olefin-based resins such as polyethylene into which insecticidal compounds are kneaded are well known, as well as the manufacturing processes therefor: that is, an insecticidal sheet is manufactured by melting and kneading a thermoplastic resin composition comprising an insecticidal compound such as an insecticide, and molding the knead mixture into a sheet or a desired shape by an ordinary molding method; and insecticidal filaments are manufactured by the melt spinning method.

It is known that such an insecticidal compound-containing thermoplastic resin is manufactured by mixing one kind of a thermoplastic resin or a thermoplastic resin mixture of two kinds of thermoplastic resins which have different solubilities to an insecticidal compound, with the insecticidal compound, and melt-kneading the resulting mixture (e.g. JP-A-4-65509 and JP-A-8-302080).

This insecticidal resin composition may be directly used as a raw material for sheets or filaments, however, in many cases, is used in the form of pellets as the thermoplastic resin composition for a master batch containing an insecticide at a high concentration, and usually, such pellets are mixed with a newly added thermoplastic resin in order to adjust the concentration of the mixture to a desired value, before the manufacturing of sheets or filaments.

In this case, the thermoplastic resin composition for the master batch and the sheets or the filaments are manufactured at different sites. Therefore, it is needed to transport the previously manufactured insecticidal compound-containing thermoplastic resin pellets for the master batch to the manufacturing site for the sheets or the filaments, and it is also needed to store such pellets over a long period of time until the distribution thereof.

However, the transportation and the storage of such pellets containing an insecticide at a high concentration have some problems. That is, because the pellets are often exposed to a high temperature atmosphere depending on the weather or the sites, transported or stored over a long period of time, the contained insecticidal compound bleeds out to the surfaces of the pellets to make the pellets sticky. Thus, the blending or the automatic blending of such pellets became markedly hard, and the insecticidal compound in the pellets evaporate, as the case may be.

DISCLOSURE OF THE INVENTION

Under such circumstances, the present inventors have made lots of efforts to develop pellets of an insecticidal resin composition, which are improved in handleability and automatic blending, since the pellets are designed to be free from the bleeding of an insecticidal compound to the surfaces thereof so as not to become sticky even under a high temperature atmosphere or during the storage over a long period of time, and also which are suitable for a mater batch capable of being easily melt-kneaded with an olefin-based resin newly added for manufacturing sheets or filaments. As a result of such efforts, the present invention has been accomplished.

The present invention provides a two-layered olefin-based resin pellet for use in an insecticidal resin composition comprising a core layer formed of an olefin-based resin composition (A) and a sheath layer formed of an olefin-based resin composition (B) and laminated on the outer surface of the core layer, wherein said olefin-based composition (A) contains an insecticidal compound, a granular inorganic filler, a metal soap, and an olefin-based resin (a) having a relatively high solubility to the insecticidal compound; and said olefin-based resin composition (B) contains, as a main component, an olefin-based resin (b) having a relatively low solubility to the insecticidal compound.

The two-layered olefin-based resin pellet of the present invention has a two-layer structure: a sheath layer of the olefin-based resin composition which contains, as the main component, the olefin-based resin having a relatively low solubility to the insecticidal compound is laminated on the outer surface of a core layer containing the insecticidal compound. Because of this two-layer structure of the pellets, the bleeding of the insecticidal compound to the surfaces of the pellets is prevented while the pellets are exposed to a high temperature atmosphere or are stored over a long period of time, and thus, the pellets do not become sticky, so that the handleability and automatic blending of the pellets are improved. Further, such pellets are easily melt-kneaded with an olefin-based resin, etc. newly added for the manufacturing of sheets or filaments. The two-layered olefin-based resin pellet of the present invention has such superior properties mentioned above.

DESCRIPTION OF REFERENCE NUMERALS

Figure 1:
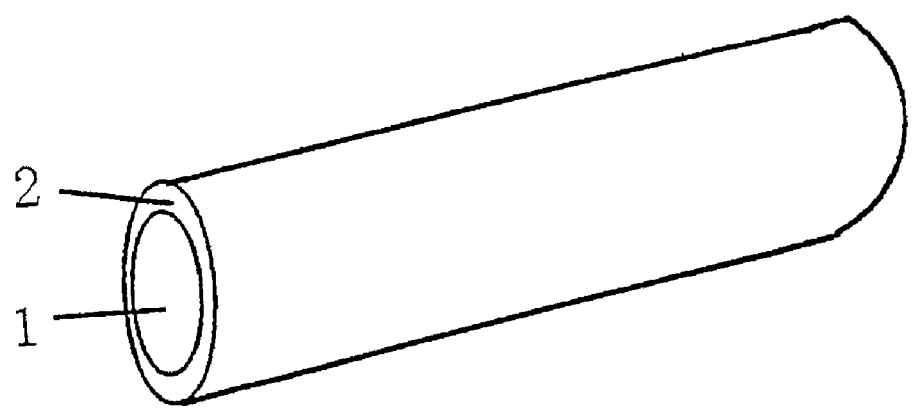
FIG. 1 is a perspective view of a two-layered olefin-based resin pellet according to the present invention.

1=a core layer, and 2=a sheath layer

BEST MODES FOR CARRYING OUT THE INVENTION

As is understood from the perspective view shown in FIG. 1, the two-layered olefin-based resin pellet for use in an insecticidal resin composition, according to the present invention, has a two-layer structure which comprises a core layer (1) of an olefin-based resin composition (A) containing an insecticidal compound, and a sheath layer (2) of an olefin-based resin composition (B) laminated on the outer surface of the core layer (1).

The core layer (1) is formed of the olefin-based resin composition (A) which contains an insecticidal compound, a granular inorganic filler, a metal soap and an olefin-based resin (a) having a relatively high solubility to the insecticidal compound.

Examples of the insecticidal compound include pyrethroids such as pyrethrin, enpenthrin, allethrin, plarethrin, d-resmethrin, d-phenothrin, cyphenothrin, permethrin, cypermethrin, cyhalothrin, cyfluthrin, bifenthrin, fenvalerate, fenpropathrin, ethofenprox, flufenprox, etc.; JH-like compounds such as methoprene, pyriproxyfen. etc.; organic phosphorous-based insecticide such as fenitrothion, etc., in addition to a variety of insecticidal compounds conventionally used in this field. Above all, pyrethroid type insecticides which are in the form of liquids at room temperatures are preferably used.

It is also possible to use not only one kind of an insecticidal compound but also two or more kinds of insecticidal compounds in combination in accordance with an end use.

Examples of the granular inorganic filler include particulate inorganic fillers such as synthesized silicates, silica, calcium carbonate, talc, clay, mica, quartz powder, diatom earth, barium sulfate, magnesium hydroxide, zinc oxide, titanium oxide, magnesium oxide and alumina, and each of these fillers may be used alone or in combination, as required.

The average particle size of the granular inorganic filler is preferably 50 µm or less, particularly 30 µm or less, since the use of a filler with too large particle size decreases the strength of the resultant filaments or sheets as final products. Since the use of a filler with too small particle size makes it hard to obtain an uniform core layer because of the flying of the filler powder in the manufacturing process, or agglomeration of the filler powder during the kneading operation, the average particle size of the filler is preferably 0.05 µm or more, particularly 0.1 µm or more. The average particle size herein referred to means a weight average particle size.

The granular inorganic filler functions as a nucleating agent which is used to provide porous filaments or sheets by drawing the filaments or sheets formed from the two-layered olefin-based resin pellets of the present invention as a raw material, and the filler as it is also functions as an adsorbing agent for the insecticidal compound. Accordingly, preferably, the filler is porous to exhibit both the functions, and the filler is preferably a porous inorganic filler which has a specific surface area of 50 $m^2/g$ or more, more preferably 50 to 800 $m^2/g$, still more preferably 50 to 500 $m^2/g$.

As such a porous inorganic filler, porous silica (balloon silica) is most preferably used among the inorganic fillers as listed above.

The metal soap functions as a bleeding accelerator for the filaments or sheets as the final products. Examples of the metal soap include well known salts of lithium, magnesium, aluminum, calcium, barium, zinc and the like with stearic acid, chlorostearic acid, lauric acid, ricinolic acid, 2-ethylhecylic acid and the like. Each of these salts may be used alone or in combination.

The wording of "having a relatively high solubility" cited from the passage "the olefin-based resin (a) having a relatively high solubility to an insecticidal compound" means that the olefin-based resin (a) has a higher solubility to the insecticidal compound than the olefin-based resin (b) forming the sheath layer (2) as described later, in the comparison between both the olefin-based resins (a) and (b). Preferably, the olefin-based resin (a) has an absolutely high solubility to the insecticidal compound. Preferred examples of such an olefin-based resin (a) include ethylene-based resins each having a density of 0.941 $g/cm^3$ or less, such as ethylene wax, low density polyethylene (LDPE), linear low density polyethylene (LLDPE), medium density polyethylene, ethylene-prolylene copolymers (EPM), ethylene-propylene-diene copolymers (EPDM), ethylene-vinyl acetate copolymers, ethylene-acrylic acid copolymers, etc., among which low density polyethylene (LDPE) having a density of 0.941 $g/cm^3$ or less, preferably 0.929 $g/cm^3$ or less, more preferably 0.90 to 0.929 $g/cm^3$, linear low density polyethylene (LLDPE) and ethylene wax are preferably used.

The core layer (1) is formed of the olefin-based resin composition (A) which essentially comprises an insecticidal compound, a granular inorganic filler, a metal soap and an olefin-based resin (a) having a relatively high solubility to the insecticidal compound, as described above. The blending ratio of the respective components is not particularly limited, and it may be appropriately selected in accordance with an end use.

When the granular inorganic filler added is small in amount, the amount of the adsorbed insecticidal compound generally becomes smaller. On the contrary, when the amount of the granular inorganic filler added is too large, the amount of the adsorbed insecticidal compound becomes larger, while the core layer tends to be fragile. For this reason, the weight ratio of the insecticidal compound to the granular inorganic filler is preferably in the range of 1:2 to 4:1.

When the amount of the metal soap is too small, the bleeding-accelerating effect becomes insufficient. However, the addition of too large amount of the metal soap does not always induce a bleeding-accelerating effect proportional to the amount thereof. Generally, the weight ratio of the insecticidal compound to the metal soap is preferably in the range of 20:1 to 1:1.

The weight ratio of the total weight of the insecticidal compound, the granular inorganic filler and the metal soap to the weight of the olefin-based resin (a) is usually in the range of 1:5 to 5:1. This is because, when the ratio of the olefin-based resin (a) is too small, the function of the resin as a binder is not sufficiently exhibited, and because, when this ratio is too large, the content of the insecticidal compound becomes smaller so that the purpose for use as the master batch for the insecticidal resin composition becomes insufficient.

If needed, the core layer (1) may contain ordinary additives such as a coloring agent, antioxidant, a variety of stabilizers, UV-absorber, antistatic agent, etc. in appropriate amounts, in addition to the above components.

The sheath layer (2) is formed of the olefin-based resin composition which mainly contains an olefin-based resin (b) having a relatively low solubility to the insecticidal compound.

The wording "relatively low solubility" herein referred to means that, in the comparison with the olefin-based resin (a) for the core layer (1), the solubility of the olefin-based resin (b) to the insecticidal compound is lower than the olefin-based resin (a). Therefore, it is preferable that the solubility of the olefin-based resin (b) to the insecticidal compound should be generally and absolutely lower, although this solubility varies according to how to use the olefin-based resin (b) in combination with the olefin-based resin (a). Preferably used as the olefin-based resin (b) is a high density polyethylene (HDPE) having a density of 0.942 $m^3/g$ or more, preferably 0.942 to 0.965 $g/cm^3$.

It is also possible to add ordinary additives such as a coloring agent, antioxidant, a variety of stabilizers, UV absorber, antistatic agent, etc. to the olefin-based resin (b), as required.

It is to be noted that the above examples of the olefin-based resins (a) and (b) are given in accordance with the general classification, and which resin is selected for use as the olefin-based resin (a) or (b) is based on the relative difference in solubility to the insecticidal compound between both the resins. For example, when a low density polyethylene or ethylene wax is used as the olefin-based resin for the core layer (1), a medium density polyethylene, which is previously given as one of the olefin-based resins (a), may be used as the olefin-based resin (b) for the sheath layer (2), since the medium density polyethylene is lower in solubility than the low density polyethylene and ethylene wax.

However, the larger the difference in solubility to the insecticidal compound between the olefin-based resins (a) and (b), the more preferable for the two-layered olefin-based resin pellets for use in an insecticidal resin composition, because the bleeding of the insecticidal compound to the surfaces of the pellets can be prevented, while the content of the insecticidal compound being increased. For this reason, the olefin-based resin (a) is preferably a low density polyethylene (LDPE), linear low density polyethylene (LLDPE) or ethylene wax, and the olefin-based resin (b) for use in combination with such an olefin-based resin (a) is preferably a high density polyethylene (HDPE).

In the olefin-based resin compositions for the core layer (1) and the sheath layer (2), the above olefin-based resins (a) and (b) are each singly used as the resin component in many cases. However, two or more kinds of olefin-based resins as a mixture may be used as the resin component in the olefin-based resin composition for the core layer or the sheath layer, in so far as the object of the present invention is not impaired.

Generally, the weight ratio of the olefin-based resin composition (A) for the core layer (1) to the olefin-based resin composition (B) for the sheath layer (2) [(A):(B)] is in the range of 10:1 to 1:5, because, when the proportion of the olefin-based resin composition for the sheath layer (2) is too small, the bleeding preventive effect of the two-layered pellets is insufficient, and because, when the proportion of the olefin-based resin composition for the sheath layer (2) is too large, the drug content of the two-layered pellets becomes smaller, which results in a disadvantage for use in a master batch.

As described above, according to the present invention, the two-layered olefin-based resin pellet for use in an insecticidal resin composition has a two-layered structure which comprises the core layer (1) formed of the olefin-based resin composition (A) which contains the insecticidal compound, and the sheath layer (2) formed of the olefin-based resin composition (B) and laminated on the outer surface of the core layer. Such two-layered olefin-based resin pellets can be readily manufactured by a known co-extrusion method and the like.

For example, the components such as the insecticidal compound, the granular inorganic filler, the metal soap, etc. are previously mixed, and this mixture and the olefin-based resin (a) are supplied from the respective supply ports to a twin-screw extruder for the core layer, while the olefin-based resin composition (B) is supplied to a single screw extruder for the sheath layer. Then, the olefin-based resin compositions (A) and (B) are supplied and extruded from the respective extruders at given temperatures through the core/sheath type die with given diameters in a predetermined weight ratio. The resulting strands of the olefin-based resin compositions are cooled and then are cut into pellets with given lengths with a pelletizer. Thus, the pellets are manufactured with ease as above.

In this method, the components such as the insecticidal compound, the granular inorganic filler and the metal soap may be mixed as follows: for example, the insecticidal compound and the granular inorganic filler are previously mixed so that the insecticidal compound can be adsorbed onto the granular inorganic filler.

The size such as diameter or length of the two-layered olefin-based resin pellets of the present invention is not limited and may be optionally selected or determined according to an end use. Generally, the diameter of the pellets is about 0.5 to about 5 mm, and the length thereof is about 1 to about 10 mm. The thickness of the sheath layer may be changed according to the diameter of the core layer and the ratio of the olefin-based resin composition (A) to the olefin-based resin composition (B), and this thickness is generally about 0.05 to about 1 mm.

The two-layered olefin-based resin pellets of the present invention as they are may be used as an insecticidal resin composition which is a raw material for insecticidal sheets or filaments, depending on the blending ratio of the respective components. In general, these pellets are preferably used as a master batch for manufacturing an insecticidal resin composition.

Such an insecticidal resin composition is easily manufactured by melt-mixing the two-layered olefin-based resin pellets of the present invention with a thermoplastic resin, preferably an olefin-based resin composition (C).

As the olefin-based resin composition (C), generally, an olefin-based resin composition which mainly contains an olefin-based resin having a low solubility to the insecticidal compound, similar to the above olefin-based resin composition (B), is used, and preferably, an olefin-based resin composition similar to the olefin-based resin composition (B) which mainly contains the olefin-based resin (b) is used.

To manufacture the insecticidal resin composition, the two-layered olefin-based resin pellets are mixed with the olefin-based resin composition (C) in such a ratio that the content of the insecticidal compound in the insecticidal resin composition can be a desired content, and this ratio is appropriately selected in consideration of a relationship with the content of the insecticidal compound in the pellets. The weight ratio of the two-layered olefin-based resin pellets to the olefin-based resin composition (C) is generally in the range of 1:1 to 15.

The insecticidal resin composition thus obtained is sheet-like extruded to obtain an insecticidal sheet, or is extruded and molded into a given shape to obtain a molded article such as an insecticidal collar or an ear tag for cattle. Especially, knitted, woven or netted fabrics made of insecticidal filaments which are obtained by melt-spinning the insecticidal resin composition can be widely used as insecticidal products such as mosquito nets.

To obtain the insecticidal filaments by melt-spinning the insecticidal resin composition, the molten insecticidal resin composition is extruded from a die, and the resultant filaments with desired diameters are cooled by an ordinary method.

The insecticidal filaments thus obtained are drawn in the lengthwise direction while being torn by the granular inorganic filler in the filaments, so that the filaments have voids therein. Such voids in the filaments also retain the insecticidal compound therein, and thus, the bleeding or the evaporation of the insecticidal compound can be controlled. As a result, the insecticidal effect of the final product is sustained far longer. Therefore, the insecticidal filaments obtained by the steps of melt-spinning and subsequent drawing are preferable.

EXAMPLES

Hereinafter, the present invention will be illustrated by way of Examples, which should not be construed as limiting the scope of the present invention in any way.

Example 1

A pyrethroid type compound (ECKTHMIN® manufactured by Sumitomo Chemical Company, Limited), porous silica (SYLYSIA 530 having an average particle diameter of 2.7 μm and a specific surface area of 500 m$^2$/g, manufactured by FUJI SILYSIA CHEMICAL LTD.), zinc stearate, titanium dioxide (a white pigment under the trade name of Tipaque CR-60 manufactured by ISHIHARA SANGYO KAISHA, LTD.) and ultramarine blue (a blue pigment) were mixed with a mixer in a ratio shown in Table 1, and the mixture was supplied to a weight-loaded feeder for powder.

The mixture (40 wt. parts) and a linear low density polyethylene resin (SUMIKATHENEO®-L G807, having a MFR of 25 g/10 mins. and a density of 0.913 g/cm$^3$, manufactured by Sumitomo Chemical Company, Limited) (30 wt. parts) were supplied to a twin-screw extruder for cores (46 φmm, and L/D=35) from the weight-loaded feeder for powder and a feeder for pellets, respectively.

On the other hand, a high density polyethylene resin (J-REX HD KL350A having a MFR of 1.1 g/10 mins. and a density of 0.951 g/cm$^3$, manufactured by Japan Polyolefins Co., Ltd.) as the component of a sheath layer was supplied to a single-screw extruder for sheath (40 φmm, and L/D=25).

The component of the core layer and the component of the sheath layer were supplied to a core/sheath type die having 6 mouthpieces from the respective extruders so that the weight ratio of the component of the core layer to the component of the sheath layer could be 70:30. The six extruded strands were allowed to pass through a water tank for cooling, and then were cut into pellets with a pelletizer. Thus, two-layered olefin-based resin pellets (3 mmφ×3.5 mm, and the thickness of the sheath layer=0.25 mm) having a pyrethroid type compound content of 15 wt. % were obtained.

In the course of this manufacturing, there was observed no pollution due to the volatilization of the drug from the core/sheath type die or no pollution due to the pyrethroid type compound in the water cooling tank.

The resultant pellets (25 kg) were packed in a paper bag and then were stored in a stockroom at a temperature of 30° C. for 24 hours, and then, the amount of the insecticidal compound bled from the surfaces of the pellets was measured. The results are shown in Table 2.

In this connection, the amount of the bled insecticidal compound in the table was measured and calculated by the following methods.

The pellets (5 g) were put in ethanol and immersed with a paint shaker for 10 minutes, and the insecticide bled from the surfaces of the pellets was eluted into ethanol. This ethanol was analyzed by a gas chromatograpy for which an analytical curve had been previously found. The amount of the insecticide dissolved in the ethanol was regarded as the amount of the insecticide bled from the surfaces of the pellets. The amount of the bled insecticide in the table was determined by calculating the ratio (weight ratio) of the weight of the bled insecticide to the weight of the insecticide in the pellets.

Comparative Example 1

A mixture (40 wt. parts) prepared in the same blending ratio shown in Table 1, and the same low density polyethylene resin (30 wt. parts) and the same high density polyethylene resin (30 wt. parts) as used in Example 1 were supplied to a twin-screw extruder from the weight-loaded feeder for powder and the feeder for pellets, respectively, and these components were extruded from the die of the extruder equipped with ordinary mouthpieces to obtain strands of the uniform knead mixture of the components. Except for these steps, single-layered pellets were obtained in the same manner as in Example 1. The resultant single-layered pellets had the same outer diameters and the same length as those of the two-layered pellets obtained in Example 1.

In the course of this manufacturing process, the evaporation of the insecticidal compound from the die of the extruder was visually observed, and it was confirmed that the cooling water tank was polluted by the pyrethroid type compound.

The amount of the bled insecticidal compound of the single-layer pellets thus obtained was evaluated in the same manner as in Example 1. The results are shown in Table 2.

TABLE 1

| Components | Amount (wt. parts) |
|---|---|
| Pyrethroid type compound | 37.5 |
| Porous silica | 37.5 |
| Zinc stearate | 12.5 |
| Titanium dioxide | 10.0 |
| Ultramarine blue | 2.5 |

TABLE 2

| | Amount of bled insecticide (%) |
|---|---|
| Example 1 | 0.1 or less |
| Comparative Example 1 | 2.5 |

Reference Example 1

The two-layered olefin-based resin pellets (14 wt. parts) obtained in Example 1 and a high density polyethylene resin (86 wt. parts) (HIZEX 5000S having a MFR of 0.8 g/10 mins. and a density of 0.954, manufactured by MITSUI CHEMICALS, INC.) were supplied to a twin-screw extruder (75 φmm, and L/D=38) and extruded to obtain an insecticidal resin composition containing 2.1 wt. % of the insecticide.

This composition was extruded through the die having 150 orifices of a monofilament molding machine of 50 φmm at 280° C., and the resulting filaments of the composition were drawn in boiling water to extend them 8 times longer. Thus, 200 denier monofilaments were obtained, and then were woven with a weaving machine to obtain a net-like fabric, and this net-like fabric was sewed to make a mosquito net.

INDUSTRIAL APPLICABILITY

The two-layered olefin-based resin pellets of the present invention as they are can be used as an insecticidal resin composition which is a raw material for insecticidal sheets or filaments. In general, such pellets of the present invention are suitably used as a master batch for manufacturing an insecticidal resin composition.

The invention claimed is:

1. A two-layered olefin-based resin pellet for use in an insecticidal resin composition comprising a core layer formed of an olefin-based resin composition (A) and a sheath layer formed of an olefin-based resin composition (B) and laminated on the outer surface of the core layer, wherein said olefin-based composition (A) contains an insecticidal compound, a granular inorganic filler, a metal soap, and an olefin-based resin (a) having a relatively high solubility to the insecticidal compound; and said olefin-based resin composition (B) contains, as a main component, an olefin-based resin (b) having a relatively low solubility to the insecticidal compound.

2. The olefin-based resin pellet according to claim 1, wherein said insecticidal compound is a pyrethroid type insecticide.

3. The olefin-based resin pellet according to claim 1, wherein, in the olefin-based resin composition (A) for the core layer, the weight ratio of the insecticidal compound to the granular inorganic filler is in the range of 1:2 to 4:1; the weight ratio of the insecticidal compound to the metal soap is in the range of 20:1 to 1:1; and the weight ratio of the total of the insecticidal compound, the granular inorganic filler and the metal soap to the olefin-based resin (a) is in the range of 1:5 to 5:1.

4. The olefin-based resin pellet according to claim 1, wherein the weight ratio of the olefin-based resin composition (A) for the core layer to the olefin-based resin composition (B) for the sheath layer ((A):(B)) is in the range of 10:1 to 1:5.

* * * * *